C
(12) United States Patent
Freerks

(10) Patent No.: US 9,782,231 B2
(45) Date of Patent: Oct. 10, 2017

(54) SURGICAL INSTRUMENT ORGANIZER

(71) Applicant: Jeffrey Freerks, Everett, WA (US)

(72) Inventor: Jeffrey Freerks, Everett, WA (US)

(*) Notice: Subject to any disclaimer, the term of this patent is extended or adjusted under 35 U.S.C. 154(b) by 0 days.

(21) Appl. No.: 14/932,947

(22) Filed: Nov. 4, 2015

(65) Prior Publication Data
US 2016/0135897 A1    May 19, 2016

Related U.S. Application Data

(60) Provisional application No. 62/076,069, filed on Nov. 6, 2014.

(51) Int. Cl.
*A61B 50/20*    (2016.01)
*A61B 50/22*    (2016.01)

(52) U.S. Cl.
CPC ............. *A61B 50/20* (2016.02); *A61B 50/22* (2016.02)

(58) Field of Classification Search
CPC ......... A47B 75/00; A61B 19/00; A61B 19/02; A61B 19/20; A61B 50/20; A61B 50/22; B25H 3/00; B25H 3/021; B25H 3/04; F16M 13/00
USPC ...................... 206/370; 211/70.6, 85.13, 184; 248/176.1; 422/297, 300
See application file for complete search history.

(56) References Cited

U.S. PATENT DOCUMENTS

| | | | | |
|---|---|---|---|---|
| 2,790,547 A * | 4/1957 | Sutton | ........................ | B01L 9/00 206/363 |
| 4,212,390 A * | 7/1980 | Raczkowski | ........ | A61B 17/105 211/85.13 |
| 5,145,655 A * | 9/1992 | Darlak | ................... | A61B 50/33 211/85.13 |
| 5,681,539 A * | 10/1997 | Riley | ........................ | A61L 2/26 206/370 |
| 6,367,637 B1 * | 4/2002 | Davis | ..................... | A61B 50/22 211/85.13 |
| 7,959,014 B2 * | 6/2011 | Dredla, IV | ............. | A61B 90/50 211/85.13 |
| 8,069,998 B2 * | 12/2011 | Thomas | ..................... | A61L 2/26 206/370 |
| 9,283,012 B2 * | 3/2016 | Brand | ................... | A61B 17/865 |

* cited by examiner

*Primary Examiner* — Bryon Gehman
(74) *Attorney, Agent, or Firm* — Jeffrey M. Furr, Esq.; Furr Law Firm

(57) ABSTRACT

This is a surgical instrument organizational device for use during medical procedures where instruments are being used. This invention is designed to hold numerous instruments upright and easily accessible. The length of the base (1) can be lengthened, shortened or heightened during manufacturing to fit the need of specialized areas of surgery all the while keeping the same basic design intact.

13 Claims, 8 Drawing Sheets

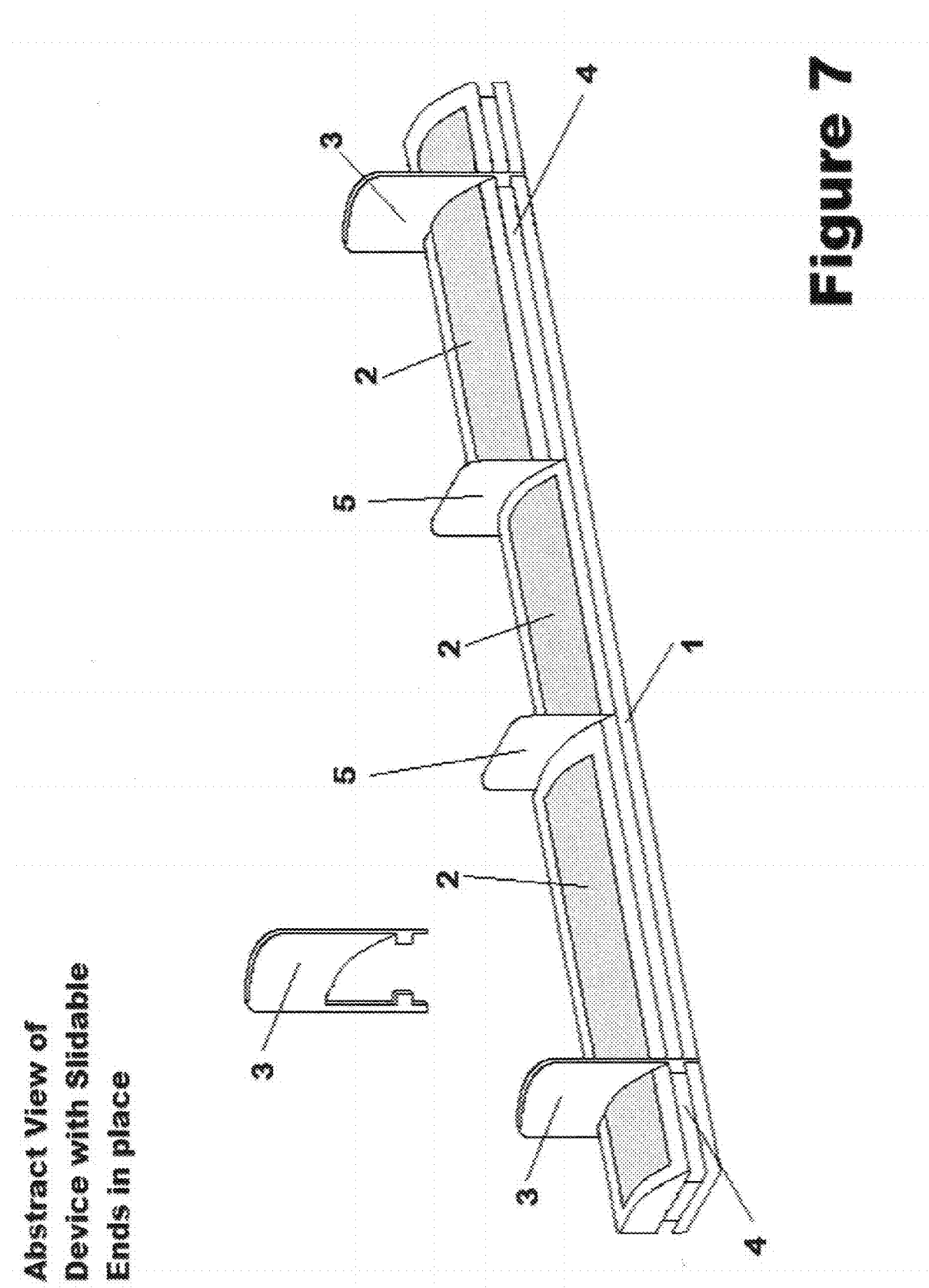

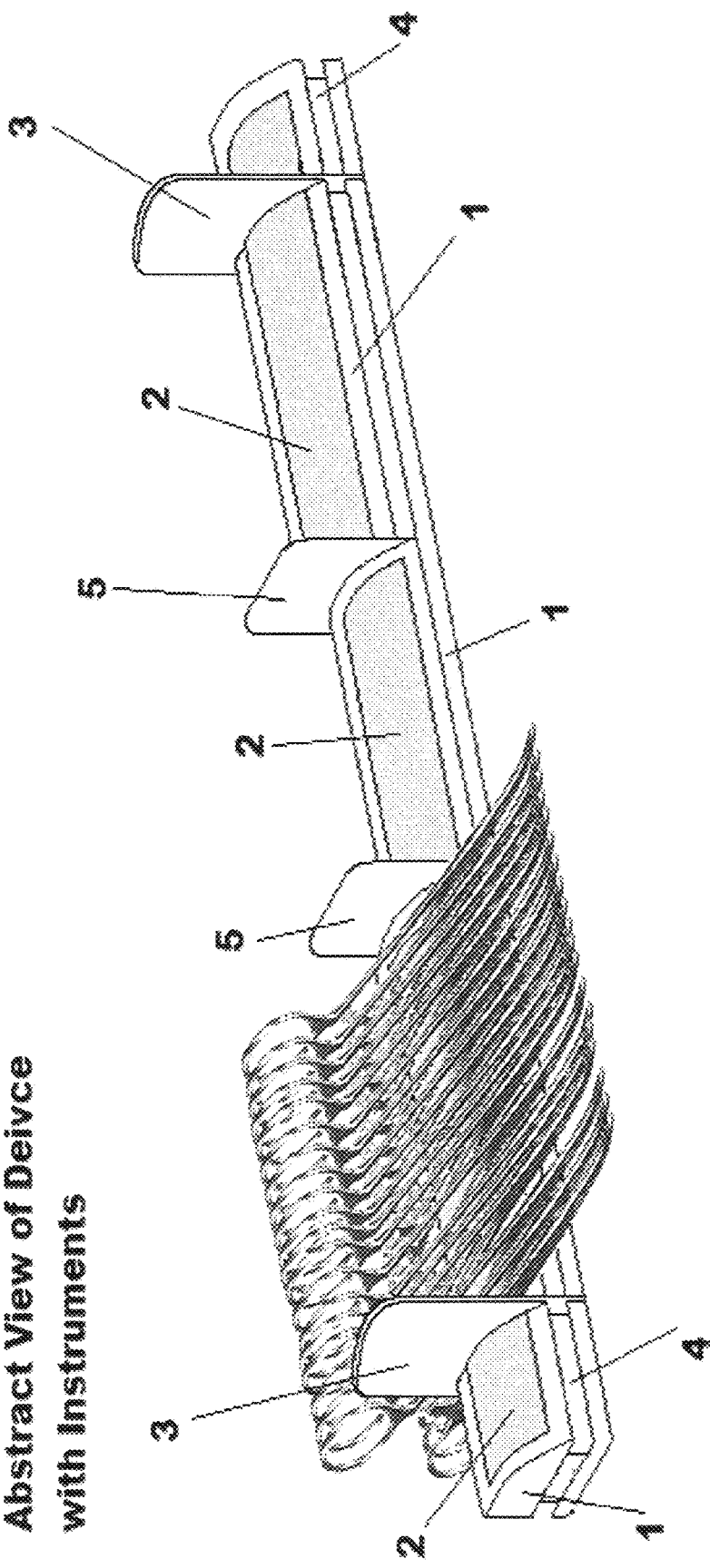

SURGICAL INSTRUMENT ORGANIZER

CROSS-REFERENCES TO RELATED APPLICATIONS

This application is the non-provisional application claiming the priority date of provisional application 62/076,069 filed Nov. 6, 2014.

BACKGROUND

This invention relates to the field of surgical medicine. More specifically, this invention is designed for superior organization of medical instruments during surgical procedures.

SUMMARY

This invention is designed to assist in keeping the surgical area organized by giving an alternative to current methods. With proper use, this will keep instruments upright and uniform.

The invention is comprised of main three pieces with five components. Affixed to the top of the base is a rubber grip to assist the side stabilizers in staying in place as well as allowing for instrument traction.

The side stabilizers slide back and forth to allow varying instrument needs. The middle section of the base is at a secondary level to allow for smaller instrument organization.

BRIEF DESCRIPTION OF THE DRAWINGS

Embodiments of the device in accordance with the present disclosure will be described with reference to the drawings, in which:

FIG. 7 is an abstract view of the device showing Slidable Instrument Ends on device.

FIG. 8 is an abstract view of the device illustrating how instruments are placed on the device.

DETAILED DESCRIPTION

Figure 1:
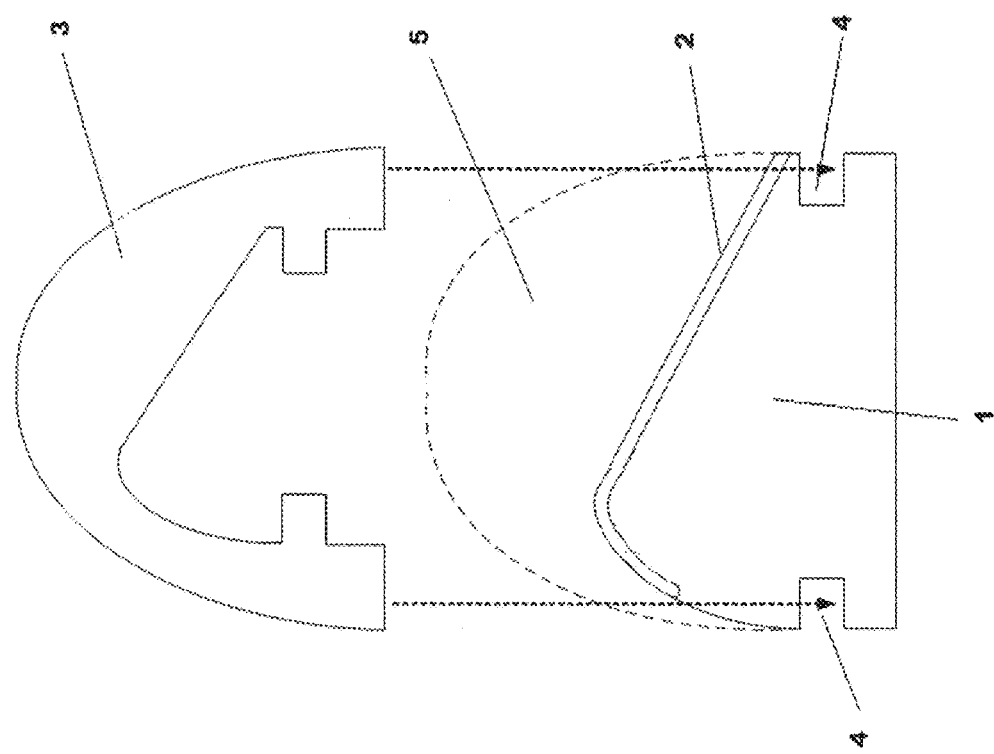
FIG. 1 is a diagram of the front view of the device indicating the vertically slidable device end, which can be inserted by the device user for the purposes of holding the surgical instruments upright or at a slight angle, depending on preference.
Figure 2:
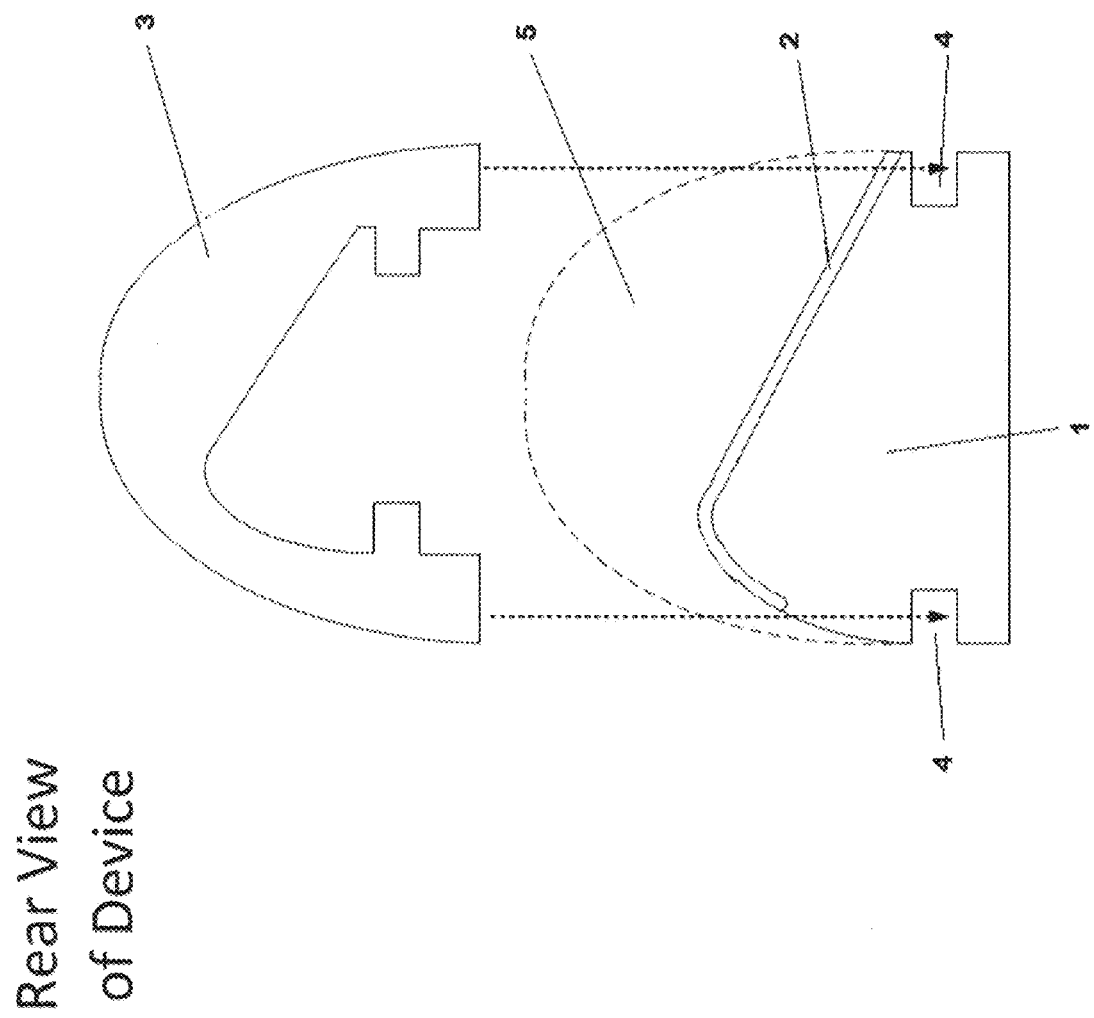
FIG. 2 is a diagram of the rear side view of the device indicating the vertically slidable device end, which can be inserted by the device user for the purposes of holding the surgical instruments upright or at a slight angle, depending on preference.
Figure 3:
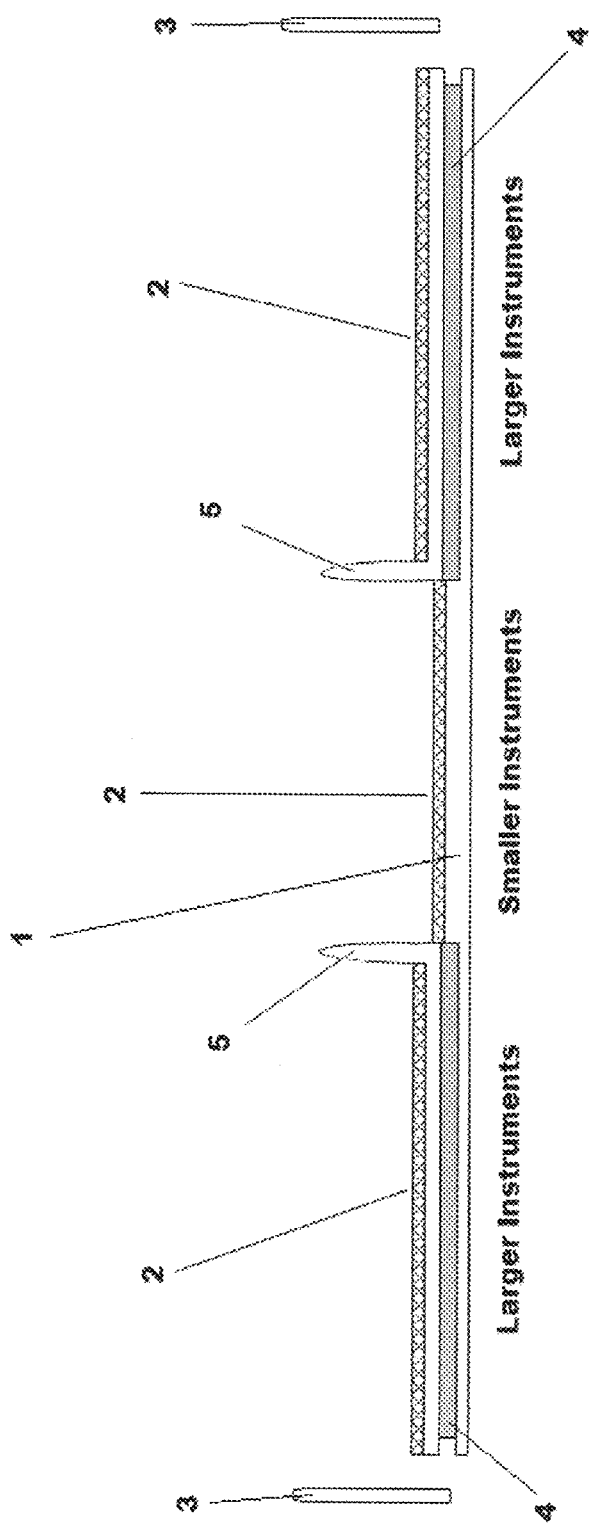
FIG. 3 is a diagram of the right side view of the device displaying the device base, slidable instrument end track, the rubber grip (for instrument stability), the designated small instrument holding area of the device, the removable device ends and the stationary device ends.
Figure 4:
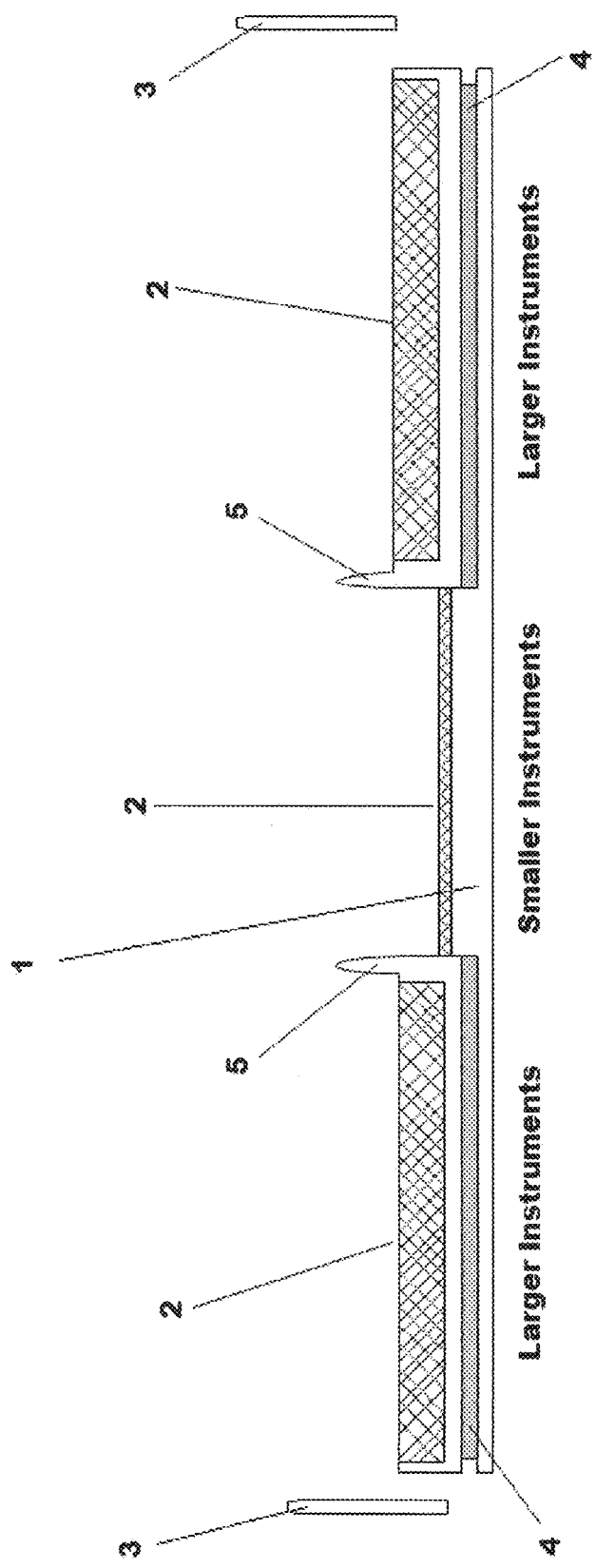
FIG. 4 is a diagram of the left side view of the device displaying the device base, the slidable instrument end track, the rubber grip (for instrument stability), the designated small instrument holding area of the device, the removable device ends and the stationary device ends.
Figure 5:
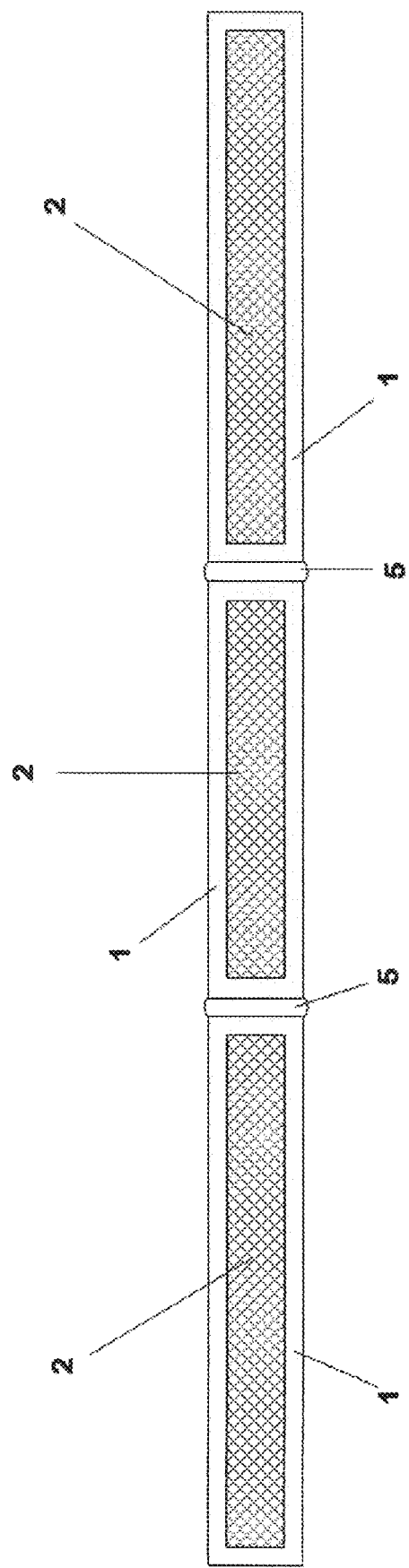
FIG. 5 is a diagram of the top view of the device displaying the user's view of the rubber grip, stationary device ends and outlying portion of the base from above the device.
Figure 6:
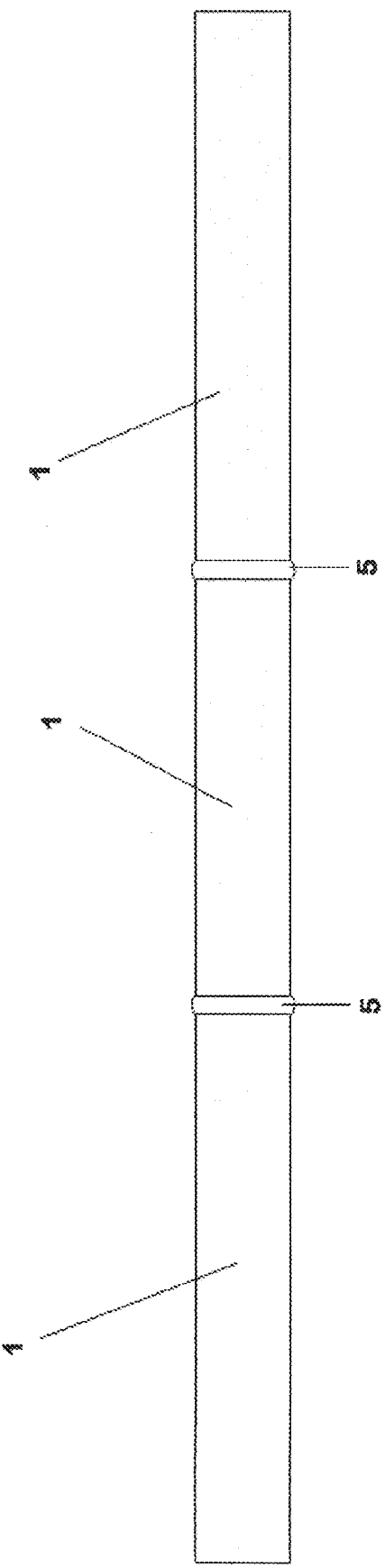
FIG. 6 is a diagram of the bottom view of the device, which displays the base and the stationary device ends.

The subject embodiments of the present invention are described here with specificity to meet statutory requirements, but this description is not necessarily intended to limit the scope of the claims.

Embodiments of the device will be described more fully hereinafter with reference to the accompanying drawings, which form a part hereof, and which show, by way of illustration, embodiments of this device. This device is intended for surgical instrumentation organization; five (5) components comprise this invention.

The base (1) of this device is set on a flat surface; note the rubber grip (2) on the top, face up, which allows for instrument and side stabilizer (3) traction. The side stabilizers (3) slide over the base (1) and into the slide guides (4) on either side (left and/or right). The design of the slide guide (4) and base (1) will allow for easy movement with minimal drag when the base (1); side stabilizers (3) are at a 90 degree angle. Tilt of the side stabilizers (3) will cause this piece to lean into the rubber grip (2), allowing for a temporary hold. Tilt of side stabilizers (3) will occur when instruments are leaning against them.

The side stabilizers (3) will have a rounded top with a back tab and front tab that are located so that they will fit into the slide guides (4) of the base (1). The side stabilizers (3) will have a cut out section that matches the shape of the top of the base (1) as to fit the base (1) properly.

The top of the base (1) will have a flat inclined surface which will face the front. This will help to stabilize the instruments that are being stored as shown in FIG. 1. This inclined surface will be covered by the rubber grip (2).

Instruments will be placed onto the device in preferred manner utilizing the higher and lower points for larger or smaller instruments. The stationary center stabilizers (5) will be at a fixed location to prevent the larger instruments from falling into the smaller instrument section of the base (1). The stationary center stabilizers (5) will be perpendicular to the base (1).

The base (1), stationary center stabilizers (5), and center guide (4) are one piece of injection molded plastic. Separately, the side stabilizers (3) are injection molded plastic. The rubber grip (2) is a thin, non-porous rubber material. With these basic materials, length, depth and height can all be easily modified during manufacturing to allow for larger or smaller sizes, while keeping the functionality the same.

The slide guides (4) can run the length of the base (1) or only a portion of it. The preferred embodiment the slide guides (4) will run from the ends of the base (1) to the stationary center stabilizers (5). The center of the base (1) can have lower height than the left and right sides of the base (1). This makes it easier to use with smaller instruments.

Length of the base (1) will be 12 inches, depth is 1 inch and height at the top of the curvature will be 1.5 inches on the Left and Right of the invention. The middle, lowered area will have a length of 3 inches (of the total 12 inches) and height of ¾ inch at the top of the curvature.

The side stabilizers (3) will be 2.5 inches total in height, 1.2 inches in depth and ⅛ inches width.

The stationary center stabilizers (5) will be 1 inch in height above the top of the base (1), ⅛ inch in width and 1 inch in depth.

The larger instruments can be stored on the left and right sides held by the side stabilizers (3)

As to a further discussion of the manner of usage and operation of the present invention, the same should be apparent from the above description. Accordingly, no further discussion relating to the manner of usage and operation will be provided.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur by those skilled in the art, it is not desired to limit the invention to the exact construction and operation shown and described, and accordingly, all suitable modifications and equivalents may be resorted to, falling within the scope of the invention.

What is claimed is:

1. A device for organizing surgical instruments, comprising:
   a generally elongated horizontal base having a planar lower surface with a front and opposite a back, said base further comprising a base left element, a base center element, and a base right element:
   said base center element having a first top surface of a first height and forming a first inclined surface facing said front of said base;
   said base left element having a second top surface of a second height and forming a second inclined surface facing said front of said base;
   said base right element having a third top surface of said second height and forming a second inclined surface facing said front of said base;
   said first inclined surface and said second inclined surfaces further including a grip element;
   a first slide guide formed at said front;
   a second slide guide formed at said back;
   a first upwardly extending and stationary center stabilizer located between said base left element and said base center element;
   a secondly upwardly extending and stationary center stabilizer located between said base right element and said base center element; and
   a pair of side stabilizers that slide over the base and into the first slide guide and the second slide guide and configured where the grip elements provide a traction to the pair of side stabilizers.

2. A device according to claim 1 further comprising having the grip elements made of rubber.

3. A device according to claim 1; wherein said first upwardly extending and stationary center stabilizer and said second upwardly extending and stationary center stabilizer each extend perpendicularly upward relative to said base.

4. A device according to claim 1 further having the pair of side stabilizers being capable of being movable laterally along the base.

5. A device according to claim 1 further comprising having the first slide and the second slide guides each having a length the same as a length of the base.

6. A device according to claim 1 further comprising having the first slide and the second slide guides each having a length shorter than a length of the base.

7. A device according to claim 1 further comprising having the first slide guides and the second slide guides are each formed only along said left base element and said right base element.

8. A device according to claim 1 further comprising having the pair of side stabilizers have a rounded top with a back tab and front tab.

9. A device for organizing surgical instruments, comprising:
   a base where the base has;
      a front;
      a top with a flat inclined surface inclined towards the front; and
      a plurality of slide guides;
   side stabilizers that slide over the base and into the slide guides;
   a top side with a grip on said top side;
   a pair of separated stationary center stabilizers;
   the side stabilizers movable along the base between a base left end and a base right end to said stationary center stabilizers;
   and,
   the side stabilizers having a rounded top with a back tab and front tab where the tabs fit into the slide guides.

10. A device according to claim 9 further comprising a grip made of rubber affixed to said flat inclined surface.

11. A device for organizing surgical instruments comprising:
   a linearly elongated horizontal base having an upper top opposite a flat, planar lower bottom and a front opposite a back and a left side opposite a right side;
   a pair of horizontally disposed slide guides formed along said front and said back;
   a left instrument holding element formed at the top left side of said base;
   a right instrument holding element formed as the top right side of said base;
   a center instrument holding element formed at the top of said base between said left instrument holding element and said right instrument holding element;
   a first upwardly disposed center stabilizer fixed between said left instrument holding element and said center instrument holding element;
   a second upwardly disposed center stabilizer fixed between said right instrument holding element and said center instrument holding element;
   a first upwardly disposed side stabilizer slidably retained within said pair of horizontally disposed slide guides at said left stabilizer element; and
   a second upwardly disposed side stabilizer slidably retained within said pair of horizontally disposed slide guides at said right stabilizer element.

12. The device of claim 11 wherein
   said right instrument holding element and said left instrument holding element each forming a top surface of a first height and forming a first inclined surface facing said front of said base; and
   said center instrument holding element further forms a top surface of a second height and forming a second inclined surface facing said front of said base;
   wherein said first height is higher than said second height.

13. A device according to claim 12 further comprising a grip made of rubber affixed to said first inclined surface and said second inclined surface.

* * * * *